US009872793B2

(12) United States Patent
Janning

(10) Patent No.: US 9,872,793 B2
(45) Date of Patent: Jan. 23, 2018

(54) APPARATUS FOR HIP AND KNEE ABDUCTION

(71) Applicant: INEW LLC, Land O Lakes, FL (US)

(72) Inventor: Spencer Janning, Loveland, OH (US)

(73) Assignee: INEW LLC, Land O Lakes, FL (US)

(*) Notice: Subject to any disclaimer, the term of this patent is extended or adjusted under 35 U.S.C. 154(b) by 0 days.

(21) Appl. No.: 15/489,359

(22) Filed: Apr. 17, 2017

(65) Prior Publication Data

US 2017/0304104 A1 Oct. 26, 2017

Related U.S. Application Data

(60) Provisional application No. 62/326,805, filed on Apr. 24, 2016.

(51) Int. Cl.
A61F 5/01 (2006.01)
A61F 5/37 (2006.01)

(52) U.S. Cl.
CPC .......... A61F 5/0193 (2013.01); A61F 5/0104 (2013.01); A61F 5/3715 (2013.01)

(58) Field of Classification Search
CPC .................................... A61F 5/0193
See application file for complete search history.

(56) References Cited

U.S. PATENT DOCUMENTS

| 5,362,305 | A | | 11/1994 | Varn | |
|---|---|---|---|---|---|
| 5,558,628 | A | * | 9/1996 | Bzoch | A61F 5/0193 128/882 |
| 6,126,624 | A | * | 10/2000 | Frauenberger | A61F 5/0193 602/23 |
| 6,254,561 | B1 | * | 7/2001 | Borden | A61N 5/1049 128/845 |
| 2008/0149116 | A1 | * | 6/2008 | Ciccantelli | A61F 5/3753 128/882 |

FOREIGN PATENT DOCUMENTS

| DE | 4438068 A1 | * | 5/1996 | ........... A61F 5/0193 |
|---|---|---|---|---|
| GB | 2133289 A | * | 7/1984 | ........... A61F 5/0193 |

* cited by examiner

Primary Examiner — Tarla Patel
(74) Attorney, Agent, or Firm — Larson & Larson, P.A.; Frank Liebenow

(57) ABSTRACT

An abductor device includes a pair of cuffs for interfacing to respective legs of a user. There is a mechanism for removably holding each cuff of the pair of cuffs to a respective leg of the user and a mechanism for maintaining a range of separation between each cuff of the pair of cuffs. This range of separation ranges from a minimum distance between each cuff of the pair of cuffs to a maximum distance between each cuff of the pair of cuffs.

20 Claims, 4 Drawing Sheets

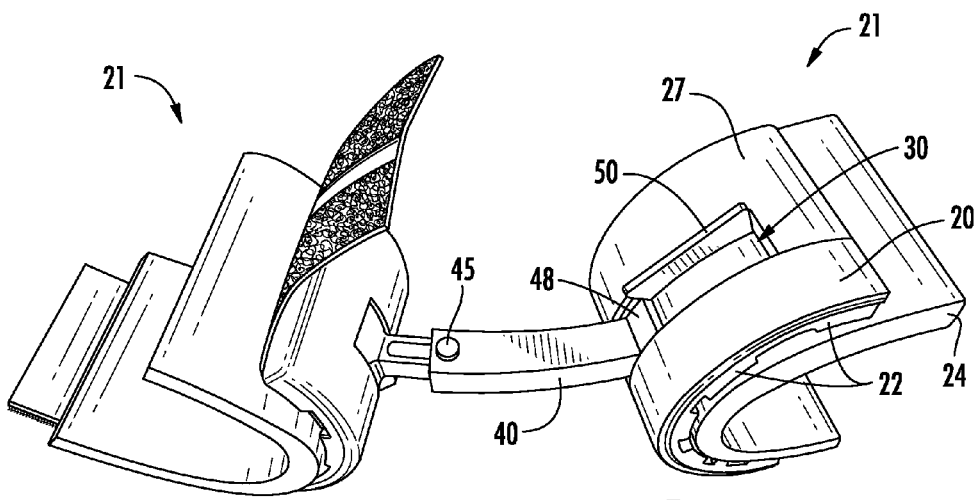
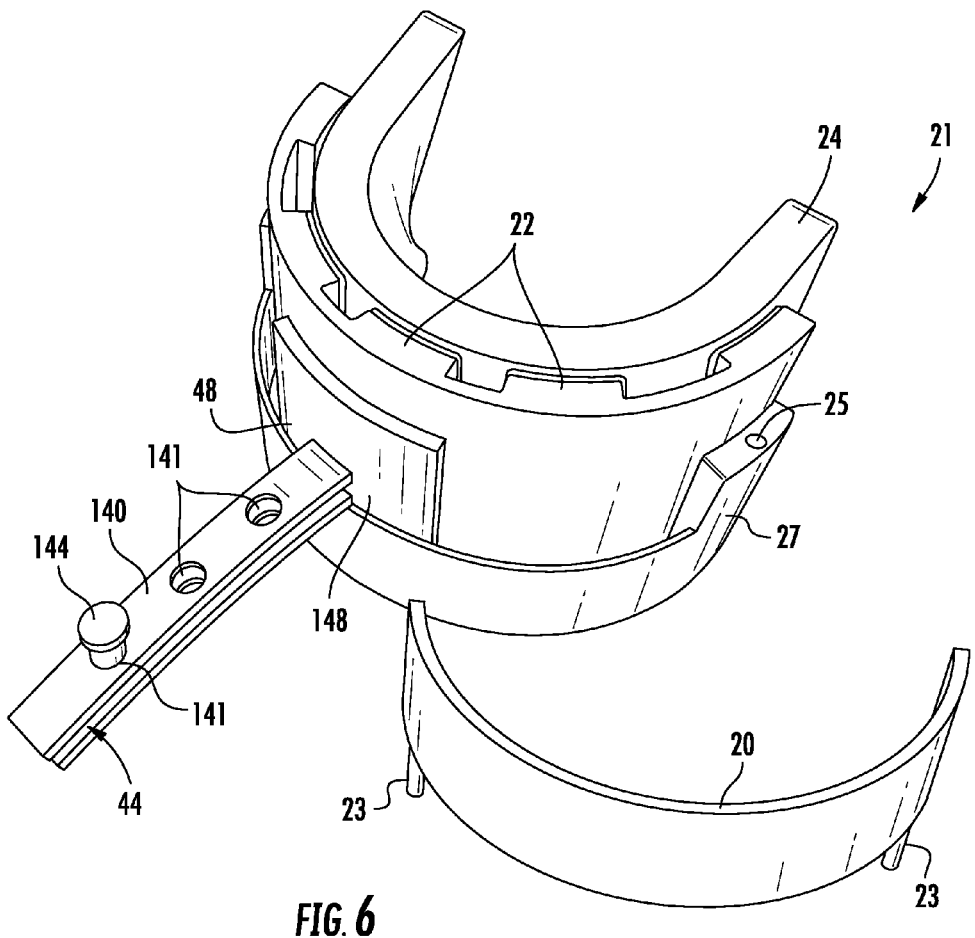

APPARATUS FOR HIP AND KNEE ABDUCTION

CROSS-REFERENCE TO RELATED APPLICATION

This application claims the benefit of U.S. provisional application No. 62/326,805 filed on Apr. 24, 2016, the disclosure of which is incorporated by reference.

FIELD

This invention relates to the field of medical devices and more particularly to a apparatus for restricting certain movements of a patient's legs.

BACKGROUND

For those who have certain medical issues such as congenital hip defects or Cerebral Palsy, or for those who have had certain types of surgery such as hip surgery, it is often desired or required to limit certain movements of their legs and to control abduction and scissoring of the legs. Prior devices used in controlling abduction and scissoring of the legs have been limited to rigid braces, wedge-shaped pillows, and leg braces with limited rotational abilities.

Rigid braces included a rigid bar separating cuffs that attach around a patient's (user's) thigh. Such rigid braces provide no ability for the patient to reposition their legs. A device called a hip and knee abductor is described in U.S. Pat. No. 5,362,305 to Varn. The hip and knee abductor disclosed in Varn is an improvement over the rigid braces, as it includes a fixed degree of angular movement of the cuffs through the use of a pivot. In the described device, there is an adjustable distance between the cuffs, but once adjusted, this distance is fixed and constant.

It has been found that the hip and knee abductor devices of the past are not comfortable for many patients as they provide no ability to move one's legs inward or outward and provide no ability to adjust the degree of angular movement of the cuffs.

What is needed is a hip and knee abductor that provides flexibility to move one's legs inward or outward and provides an adjustable degree of angular movement.

SUMMARY

In one embodiment, an abductor device is disclosed. The abductor device includes a pair of cuffs for interfacing to respective legs of a user. A first arm having a hollow channel is slideably interfaced to a first cuff of the pair of cuffs. A second arm is slideably interfaced to a second cuff of the pair of cuffs. The second arm has a closed channel and telescopedly fitting within the hollow channel of the first arm. A pin passes through the first arm and engages with the closed channel, thereby providing a range of separation distance between the cuffs.

In another embodiment, an abductor device is disclosed. The abductor device includes a pair of cuffs for interfacing to respective legs of a user. There is a mechanism for removably holding each cuff of the pair of cuffs to a respective leg of the user and a mechanism for maintaining a range of separation between each cuff of the pair of cuffs. This range of separation ranges from a minimum distance between each cuff of the pair of cuffs to a maximum distance between each cuff of the pair of cuffs.

In another embodiment, an abductor device is disclosed including a pair of cuffs for interfacing to respective legs of a user. A first arm has a first arm base at one end and a hollow channel starting at a distal second end. The first arm base slideably interfaces into a first rotation channel of a first cuff of the pair of cuffs. A second arm has a second arm base at one end and a closed channel. The second arm base slideably interfaces into a second rotation channel of a second cuff of the pair of cuffs. The second arm telescopedly fits within the hollow channel of the first arm providing for a range of separation between the first cuff and the second cuff. A pin passes through the distal second end of the first arm and engages with the closed channel of the second arm, thereby providing a limit to the range of separation distance between the cuffs.

BRIEF DESCRIPTION OF THE DRAWINGS

The invention can be best understood by those having ordinary skill in the art by reference to the following detailed description when considered in conjunction with the accompanying drawings in which:

FIG. 5 illustrates a top perspective view of a hip and leg abductor in a retracted position.

FIG. 6 illustrates a perspective view of a cuff of the hip and leg abductor with an alternate, limiting extension channel.

DETAILED DESCRIPTION

Figure 1:
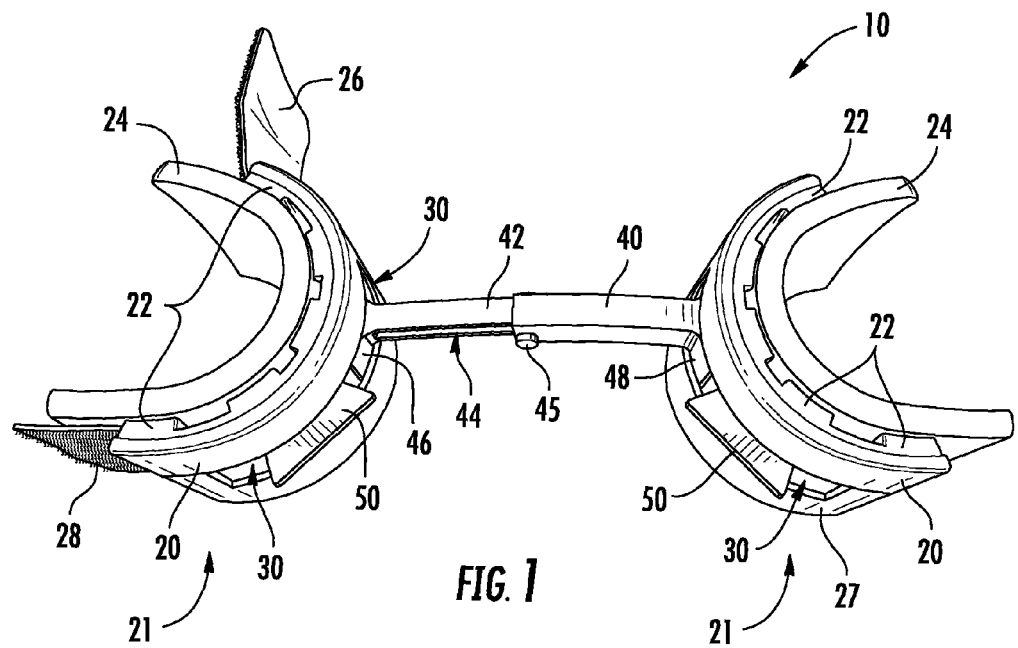
FIG. 1 illustrates a perspective view of a hip and leg abductor in an extended position.

Reference will now be made in detail to the presently preferred embodiments of the invention, examples of which are illustrated in the accompanying drawings. Throughout the following detailed description, the same reference numerals refer to the same elements in all figures.

Throughout the following detailed description, a user, patient, or wearer is used to refer to one who uses the disclosed device.

Figure 2:
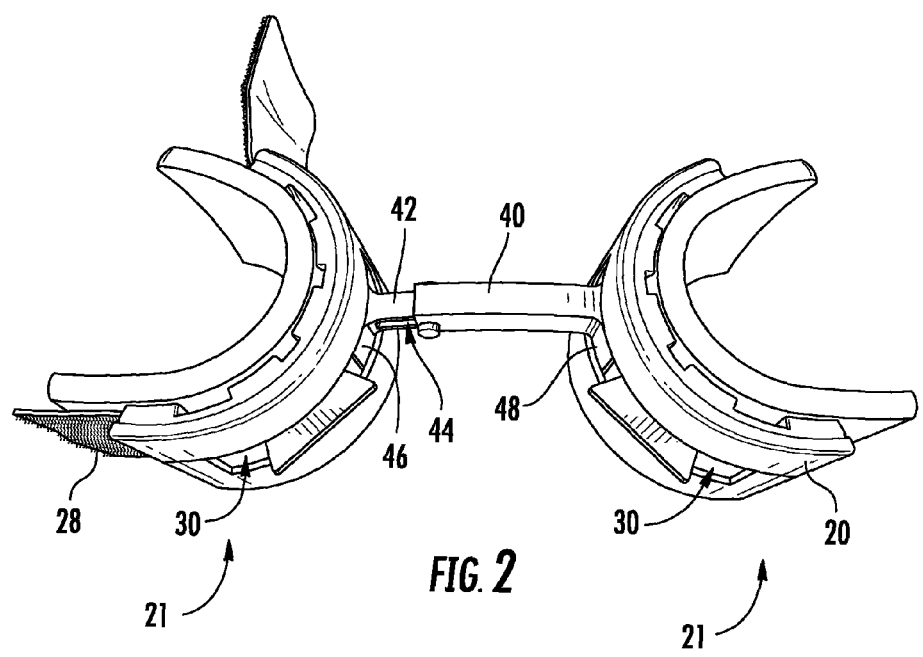
FIG. 2 illustrates a perspective view of a hip and leg abductor in a retracted position.

Referring to FIGS. 1 and 2, perspective views of a hip and leg abductor 10 are shown in an extended position (FIG. 1) and in an retracted position (FIG. 2). The hip and leg abductor 10 includes two cuffs 21 connected to each other by a telescoping set of arms 40/42 (e.g. the arms 40/42 are telescopedly interfaced to each other). The telescoping arms 40/42 provide a mechanism for maintaining a range of distance between each cuff between a minimum distance and the maximum distance. The arms 40/42 provide a degree of telescoping such that a user's legs are able to move a pre-determined distance in an opening/closing direction.

Each cuff 21 includes a cushion 24 on the inside surface of the cuff 21 that is held to the cuff 21 by one or more pads 22 made of hook material, as the cushions 24 are generally made of a cloth or felt-like material that removably adheres to the hook material of each pad 22. In this way, the cushions 24 are removable and replaceable as they wear or become soiled.

Each cuff 21 includes a mechanism for attaching/holding the cuff 21 to a user. As it is expected that the user will want to remove the cuffs 21 during some periods of the day, the mechanism for attaching/holding the cuff 21 to a user is preferably removable. In the examples shown, the mechanism for holding the cuff 21 to the user includes a sheet of hook material 26 that removably interfaces with a sheet of loop material 28, though any form of mechanism for holding the cuff 21 to the user is anticipated, for example, a buckle mechanism, one or more snaps, one or more buttons, etc.

The arms 40/42 interface to respective cuffs 21 within a rotation channel 30 in a base portion 27 of each cuff 21. A base 48 of a first arm 40 is slideably interfaces to the rotation channel 30 of one cuff 21 and a base 46 of the second arm 42 slideably interfaces to the rotation channel 30 of the other cuff 21. This slideable interface allows for rotation of each cuff 21 with respect to the other cuff 21 as the bases 46/48 of the arms 40/42 travel along the rotation channels 30 of respective cuffs 21, providing a mechanism for rotation of each cuff 21 with respect to the other cuff 21. This travel is limited by the length of the rotation channels 30 of, alternately, as is shown in detail in FIGS. 3 and 4, the travel is further limited by the introduction of angular movement limiting adjuster tabs 50.

The second arm 42 slides in/out of a hollow channel within the first arm 40 in the embodiments shown. The base 48 of the first arm 40 is formed at one end of the first arm 40 and the hollow channel is formed at a distant second end of the first arm 40.

In a preferred embodiment, the second arm 42 has a closed channel 44 (e.g. a channel that is closed at both ends like a slot) that is traversed by a pin 45 that is installed into an end of the first arm 40. In this way, as the second arm 42 slides to the greatest length of extension, the closed channel 44 stops as a closed end of the closed channel 44 butts up against the pin 45. This provides a range of spacing between the cuffs 21 limited by the length of the closed channel 44. In this way, the second arm 42 slides out the first arm 40 until the closed end of the closed channel 44 reaches the pin 45 as shown in FIG. 1 and the second arm 42 slides into the first arm 40 until the closed end of the closed channel 44 reaches an internal end of the cavity of the first arm 40 or an end of the first arm 40 reaches the cuff 21 and/or base 46 of the second arm 42, as shown in FIG. 2. As will be shown with FIG. 6, in some embodiments, the amount of closure is limited by adjustable limiting stops 141.

Figure 3:
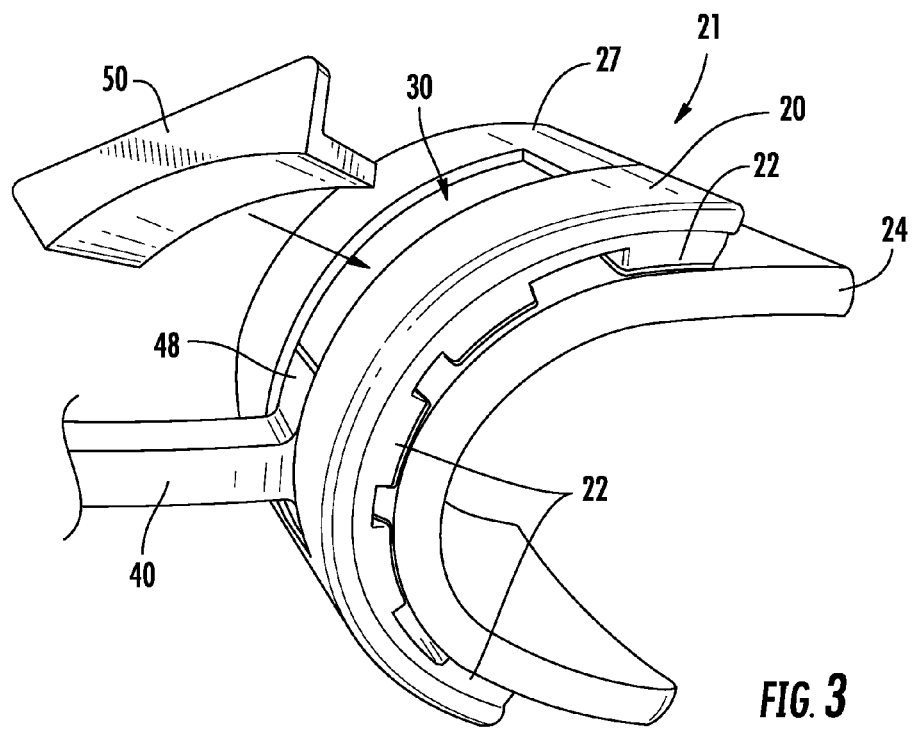
FIGS. 3 and 4 illustrate perspective views of a cuff of a hip and leg abductor modified with angular movement limiting adjuster.
Figure 4:
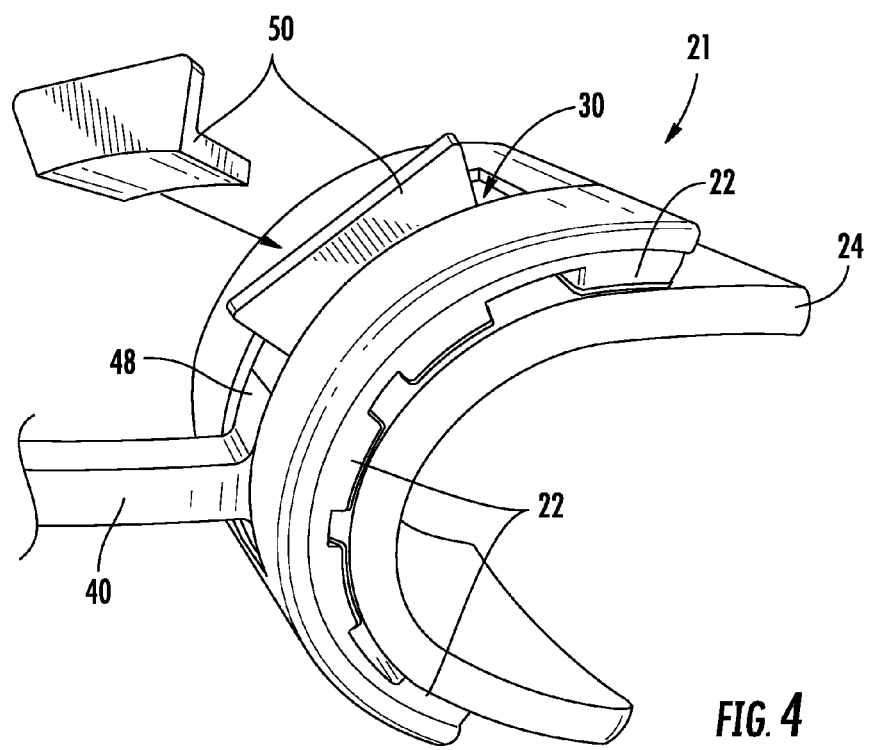

Referring to FIGS. 3 and 4, perspective views of a cuff 21 of the hip and leg abductor 10 modified with angular movement limiting adjuster tabs 50. For brevity, only one of the two cuffs 21 is shown, though the other cuff of the two cuffs 21 is generally symmetrical.

Without the angular movement limiting adjuster tabs 50, the base 48 of the first arm 40 is free to traverse the full length of the rotation channel 30 in the respective cuff 21. Should the user (e.g. patient) require more restrictive rotational movement, one or more angular movement limiting adjuster tabs 50 are inserted into the rotation channel 30 as shown in FIGS. 3 and 4. It is fully anticipated that the angular movement limiting adjuster tabs 50 be sized and labeled to provide specific degrees of rotation (when inserted into the rotation channels 30) and multiple sizes of angular movement limiting adjuster tabs 50 are anticipated to meet the needs of various users.

Figure 7:
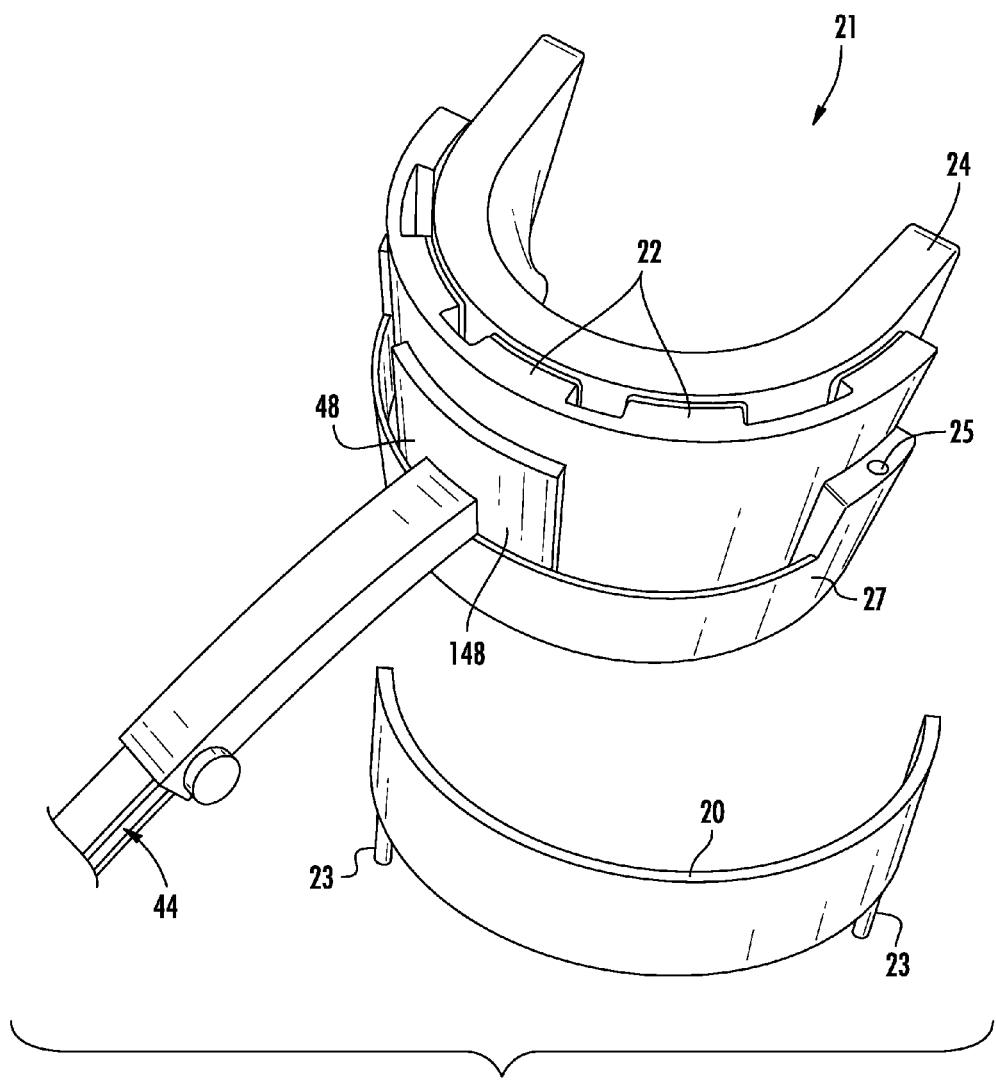
FIG. 7 illustrates a perspective view of a cuff of the hip and leg abductor with a non-limiting extension channel.

In some embodiments, the angular movement limiting adjuster tabs 50 are held within the rotation channel 30 by friction and/or gravity while in other embodiments, the angular movement limiting adjuster tabs 50 are held within the rotation channel 30 by a removable cover portion 20 (see FIGS. 6 and 7).

Referring to FIG. 5, the hip and leg abductor 10 is shown from the top in a retracted position. Note that although not required, the arms 40/42 are curved in an arc to provide an angle of required rotation as the wearer's legs are moved apart/together. An arc of the second arm 42 is substantially congruent to an arc of the first arm 40.

Referring to FIG. 6, a cuff of the hip and leg abductor 10 is shown with an alternate second arm 140 having adjustable limiting stops 141 along the closed channel 44. The adjustable limiting stops 141 provide a mechanism for adjusting the minimum distance between the cuffs 21. As it is anticipated that, for some user's, it is desired to limit how close that user is able to close their legs. For such, the embodiment shown in FIG. 6 has an alternate second arm 140 having adjustable limiting stops 141 (shown as three stops, though any number is anticipated) along the closed channel 44. A limit-adjustment pin 144 is inserted into any one of the adjustable limiting stops 141 to limit travel of the alternate second arm 140 as it enters the first arm 40.

Also shown in FIG. 6 is a removable cover portion 20 for configuring the cuff 21. The base 48 of the alternate second arm 140 is shown inserted into the rotation channel 30 and the optionally removable cover portion 20 is shown removed to allow removing/changing, for example, between the alternate second arm 140 and the second arm 42. In this way, it is also possible to exchange the angular movement limiting adjuster tabs 50 if needed due to an alternate embodiment of the base portion of the angular movement limiting adjuster tabs 50 having extensions into both sides of the rotation channel 30.

In some embodiments, the removable cover portion 20 is held to the cuff 21 by an adhesive applied during manufacture, by a physician/technician, or by an end user. In some embodiments, the removable cover portion 20 is held to the cuff 21 by pegs 23 that fit tightly into holes 25 of the cuff 21.

In FIG. 7, the cuff of the hip and leg abductor 10 is shown with the first arm 40 inserted into the rotation channel 30, ready for the removable cover portion 20 to be attached.

In some embodiments, the hook material 26 and/or the loop material 28 are interfaced to the base of the cuff 21 by an elastic material providing for improved comfort to the user/wearer.

In use, the degree of abduction is controlled by the length of the closed channel 44 and the depth of the inner channel of the first arm 40. These dimensions control the maximum separation distance and the minimum separation distance between the cuffs 21. In embodiments having adjustable limiting stops 141, the minimum separation distance between the cuffs 21 is, optionally, further limited by the insertion of the limit-adjustment pin 144 into one of the adjustable limiting stops 141, thereby limiting the minimum distance between the cuffs 21.

In a preferred embodiment, the arms 40/42/140 have an arc shape for added comfort of the wearer.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. An abductor device comprising:
a pair of cuffs for interfacing to respective legs of a user;
a first arm slideably interfaced to a first cuff of the pair of cuffs such that the first cuff rotates in an arc with respect to the first arm, the first arm having a hollow channel;
a second arm slideably interfaced to a second cuff of the pair of cuffs such that the second cuff rotates with respect to the second arm, the second arm having a closed channel and the second arm telescopedly fitting within the hollow channel of the first arm; and
a pin passing through the first arm and engaging with the closed channel, thereby providing a range of separation distance between the cuffs;
whereas the first cuff rotates with respect to the second cuff.

2. The abductor device of claim 1, wherein the first arm is slideably interfaced to the first cuff in a first rotation channel formed lengthwise around a perimeter of the first cuff.

3. The abductor device of claim 1, wherein the second arm slideably interfaced to the second cuff in a second rotation channel formed lengthwise around a perimeter of the second cuff.

4. The abductor device of claim 1, further comprising means for removably holding on each of the cuffs, the means for removably holding for engaging each cuff of the pair of cuffs to the respective leg of the user.

5. The abductor device of claim 4, wherein the means for removably holding comprises a first sheet of hook material affixed to one end of the first cuff that removably mates with a first sheet of loop material affixed to a second end of the first cuff, and a second sheet of hook material affixed to one end of the second cuff that removably mates with a second sheet of loop material affixed to a second end of the second cuff.

6. The abductor device of claim 1, further comprising a cushion held against an inside surface of each of the two cuffs.

7. The abductor device of claim 6, wherein the cushion is held to the inside surface of each of the two cuffs by at least one pad of hook material for removal and replacement of the cushion.

8. The abductor device of claim 1, further comprising at least one adjustable limiting stop formed in the second arm.

9. The abductor device of claim 8, further comprising a limit-adjustment pin inserted into one of the at least one adjustable limiting stops formed in the second arm, the limit-adjustment pin limiting a minimum distance between the cuffs of the abductor device.

10. The abductor device of claim 1, wherein the first arm and the second arm are arced, thereby holding the first cuff at a non-zero angle with respect to the second leg cuff.

11. An abductor device comprising:
a pair of cuffs for interfacing to respective legs of a user;
means for removably holding, the means for removably holding for engaging each cuff of the pair of cuffs to a respective leg of the user;
means for maintaining a range of separation between each cuff of the pair of cuffs, the range of separation ranging from a minimum distance between each cuff of the pair of cuffs and a maximum distance between each cuff of the pair of cuffs;
wherein a first base portion at one end of the means for maintaining a range of separation interfaces to a first cuff of the pair of cuffs in a first rotation channel that is formed lengthwise around a perimeter of in the first cuff; and
wherein a second base portion at a distal end opposing the one end of the means for maintaining a range of separation interfaces to a second cuff of the pair of cuffs in a second rotation channel that is formed lengthwise around a perimeter of in the second cuff.

12. The abductor device of claim 11, wherein the means for maintaining a range of distance between each cuff comprises a pair of arms that are telescopingly interfaced, a first arm of the pair of arms is affixed to a first cuff of the pair of cuffs and a second arm of the pair of arms is affixed to a second cuff of the pair of cuffs, the arms telescope to provide the range of separation between the cuffs from the minimum distance to the maximum distance.

13. The abductor device of claim 12, further comprising means for adjusting the minimum distance between the cuffs.

14. The abductor device of claim 12, wherein the means for removably holding comprises hook and loop material.

15. The abductor device of claim 11, wherein means for maintaining a range of separation between each cuff of the pair of cuffs is curved.

16. An abductor device comprising:
a pair of cuffs for interfacing to respective legs of a user;
a first arm having a first arm base portion at one end and a hollow channel starting at a distal second end, the first arm base portion of the first arm slideably interfaced into a first rotation channel of a first cuff of the pair of cuffs, the first rotation channel formed around an outside surface of the first cuff;
a second arm having a second arm base portion at one end and a closed channel, the second arm base portion of the second arm slideably interfaced into a second rotation channel of a second cuff of the pair of cuffs, the second rotation channel formed around an outside surface of the second cuff, the second arm telescopedly fitting within the hollow channel of the first arm; and
a pin passing through the distal second end of the first arm and engaging with the closed channel of the second arm, thereby providing a range of separation distance between the cuffs.

17. The abductor device of claim 16, further comprising a first sheet of hook material affixed to one end of the first cuff that removably mates with a first sheet of loop material affixed to a second end of the first cuff, and a second sheet of hook material affixed to one end of the second cuff that removably mates with a second sheet of loop material affixed to a second end of the second cuff.

18. The abductor device of claim 16, further comprising at least one adjustable limiting stop formed in the second arm.

19. The abductor device of claim 18, further comprising a limit-adjustment pin inserted into one of the at least one adjustable limiting stops formed in the second arm, the limit-adjustment pin limiting a minimum distance between the cuffs of the abductor device.

20. The abductor device of claim 16, wherein the first arm and the second arm are arced, thereby holding the first cuff at a non-zero angle with respect to the second leg cuff.

* * * * *